US009594011B2

(12) United States Patent
Herzog

(10) Patent No.: US 9,594,011 B2
(45) Date of Patent: Mar. 14, 2017

(54) METHOD AND INSTRUMENTATION FOR DETERMINING A PHYSICAL PROPERTY OF A PARTICLE

(75) Inventor: William D. Herzog, Groton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1750 days.

(21) Appl. No.: 12/124,767

(22) Filed: May 21, 2008

(65) Prior Publication Data

US 2009/0316138 A1    Dec. 24, 2009

Related U.S. Application Data

(60) Provisional application No. 61/125,534, filed on Apr. 25, 2008.

(51) Int. Cl.
| | | |
|---|---|---|
| G01N 33/50 | (2006.01) | |
| G01N 15/14 | (2006.01) | |
| G01N 21/53 | (2006.01) | |
| G01N 21/35 | (2014.01) | |
| G01N 21/47 | (2006.01) | |
| G01N 21/3577 | (2014.01) | |

(52) U.S. Cl.
CPC ......... G01N 15/1456 (2013.01); G01N 21/53 (2013.01); G01N 21/35 (2013.01); G01N 21/3577 (2013.01); G01N 2021/4707 (2013.01); G01N 2021/4709 (2013.01); G01N 2021/4726 (2013.01)

(58) Field of Classification Search
None
See application file for complete search history.

(56) References Cited

U.S. PATENT DOCUMENTS

| | | | |
|---|---|---|---|
| 4,415,265 A * | 11/1983 | Campillo et al. | ............. 356/338 |
| 6,417,920 B1 | 7/2002 | Shimaoka | |
| 6,469,786 B2 | 10/2002 | Shimaoka | |
| 7,106,442 B2 | 9/2006 | Silcott et al. | |
| 7,126,687 B2 | 10/2006 | Hill et al. | |
| 7,538,869 B2 * | 5/2009 | Treado et al. | ................ 356/301 |
| 2001/0055462 A1 * | 12/2001 | Seibel | ............................ 385/147 |
| 2002/0137993 A1 * | 9/2002 | Pickard | ......................... 600/310 |
| 2007/0165216 A1 * | 7/2007 | Haridas | .......................... 356/301 |

OTHER PUBLICATIONS

Experiment 3 paper: Gas Phase Analysis of Air Components and Air Pollutants Using FTIR CH3420: Environmental Chemistry, Plymouth State University.*
Green, R. E., et al. "Flow Cytometric Determination of Size and Complex Refractive Index for Marine Particles: Comparison with Independent and Bulk Estimates," *Applied Optics*: 42(3): 526-541 (2003).
Szymanski, W.W., et al., "A New Method for the Simulatneous Measurement of Aerosol Particle Size, Complex Refractive Index and Particle Density," *Meas. Sci. Technol.*: 13: 303-397 (2002).

* cited by examiner

*Primary Examiner* — Jason Sims
(74) *Attorney, Agent, or Firm* — Hamilton, Brook, Smith & Reynolds, P.C.

(57) ABSTRACT

Physical property determination of a particle or classification of the particle as a function of the physical property by evaluating scattered light profile from a single particle is disclosed. The particle may include chemical structures that vibrate as a function of a physical property of the particle. The physical property may include an absorptive property of the particle or a chemical composition. From a detected scattered light spectrum, at least two anomalous dispersive regions may be identified. The physical property of the particle may be determined as a function of the at least two regions. A system employing the physical property determination can achieve sensitivities useful for low particle density applications such as detection for biological and chemical agents.

15 Claims, 12 Drawing Sheets

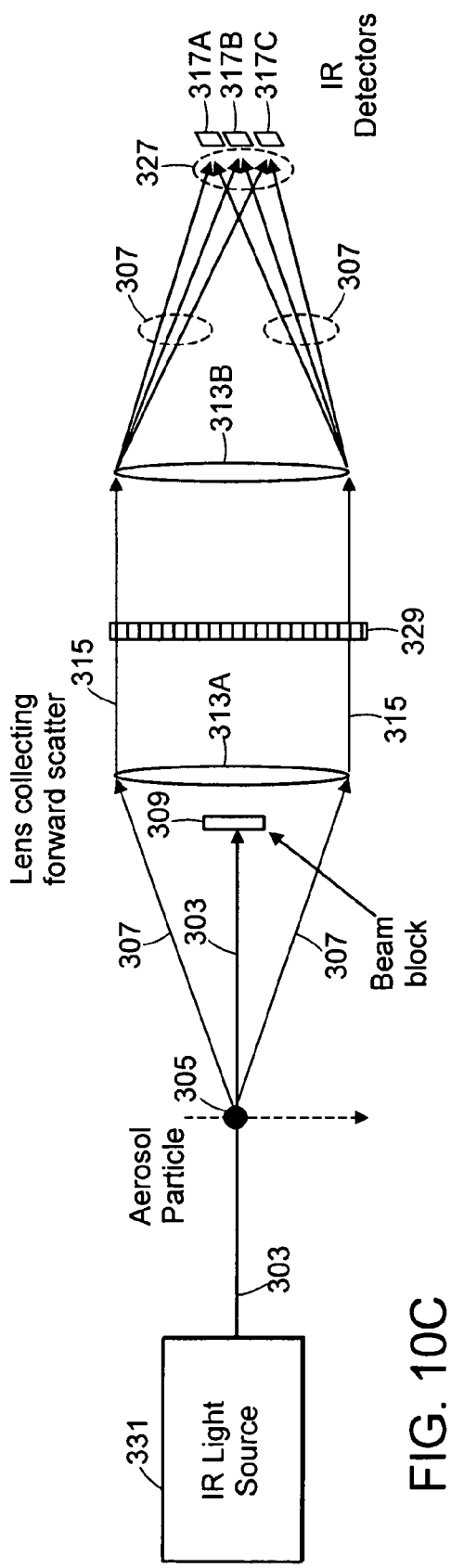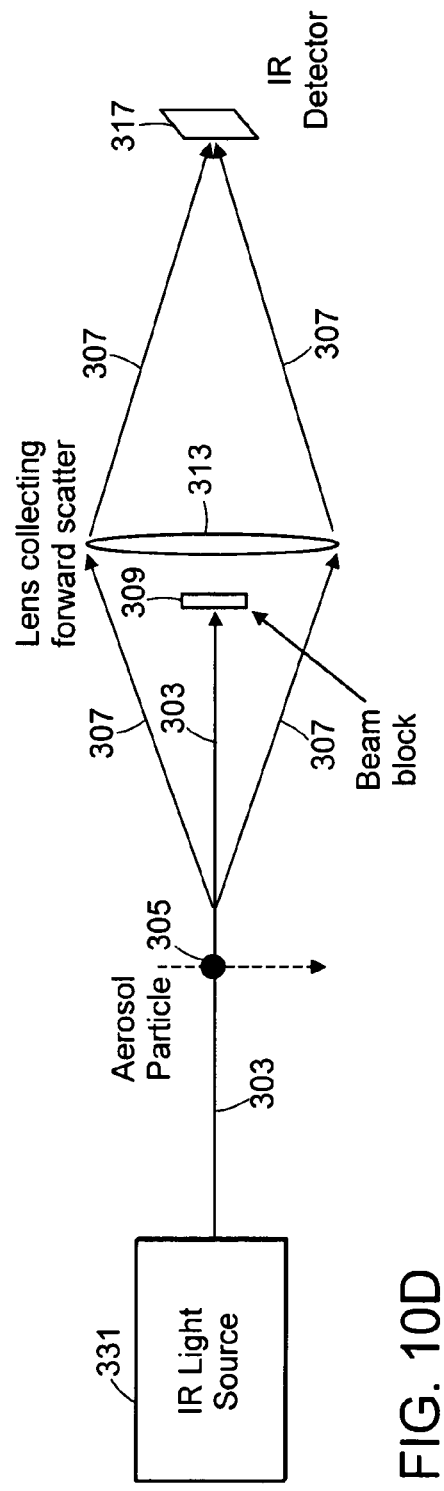
FIG. 10C
FIG. 10D

METHOD AND INSTRUMENTATION FOR DETERMINING A PHYSICAL PROPERTY OF A PARTICLE

RELATED APPLICATION

This application claims the benefit of U.S. Provisional Application No. 61/125,534, filed on Apr. 25, 2008, entitled "Method and Instrumentation for Determining a Physical Property of a Particle." The entire teachings of the above application is incorporated herein by reference.

GOVERNMENT SUPPORT

The invention was supported, in whole or in part, by a grant FA8721-05-C-0002 from United States Air Force. The Government has certain rights in the invention.

BACKGROUND

The detection and discrimination of biological aerosols from an ambient aerosol became a heightened concern during first Gulf War with Iraq in 1991. As a result of this perceived threat, the development of biological aerosol detectors for use as triggers in a system context began in earnest. The flurry of activity to develop this capability is evidenced by various works published in the United States, United Kingdom, and Canada.

Aerosol sensors that were being developed and field-tested were a departure from the instruments that had been developed for much of aerosol science in previous decades. Present day needs typically require very small concentrations of biological aerosols to be detected. For example, single aerosol particles in a liter of air, in a background of a very large number of ambient aerosol particles, or 100's to 1000's of particles per liter of air. The first instruments of this type simply measured the particle size through optical scattering or aerodynamic means. Rapid advances included measuring the particle shape in addition to size and measuring a fluorescent light scatter in multiple bands, with or without measurement of particle size.

SUMMARY

Due to the present day needs of detection systems, instruments designed to measure individual aerosols particles one at a time in a very rapid fashion rather than measuring mixtures, or ensembles, of aerosol particles, are needed. There is also a need to meet the challenge for on-the-fly aerosol sensor developers, which is to apply more discriminating techniques, such as vibrational spectroscopy, to individual aerosol particles in a manner consistent with rapid analysis. There is also a need to develop instruments that can detect and discriminate types of aerosols in addition to biological aerosols.

In example embodiments, a system, and corresponding method, which replaces the complexity of an imaging system requiring a multi-element detector with one, or a small number, of detectors that collect all of the infrared light scattered in an appropriate direction is presented. Using example embodiments of the system presented herein, the scattered light may be produced by a single particle to utilize on-the-fly aerosol detection.

The system may be configured to determine a physical property of a particle. The particle may be a simple particle or a complex particle, for example a DNA strand, and the vibrational excitation may include low energies, for example energies lower than 0.5 eV. The physical property of the particle may be a chemical composition and/or an absorption region. The system may include a light detector that may be configured to detect scattered light from a particle, where the particle may have chemical structures that vibrate as a function of the physical property of the particle. The system may also include an identifying unit that may be configured to identify at least two regions of a spectrum of the scattered light that may be based on vibrations of the chemical structures. The chemical bonds may vibrate with vibrational excitation energies less than 0.5 eV. The system may further include a determination unit that is configured to determine the physical property of the particle as a function of the at least two regions.

The determination unit may be further configured to classify the particle. The determination unit may also be configured to identify the at least two regions by identifying a region in the spectrum of the scattered light having a non-decrease of intensity with increasingly longer wavelengths. The determination unit may also be configured to determine the physical property of a single particle by analyzing the scattered light produced solely by the single particle.

The system may further include a light source that may be configured to produce light in a direction of propagation to illuminate the particle resulting in the scattered light. The light source may be an infrared light source configured to generate wavelengths greater than 2.5 µm. The light source may further be configured to generate the at least two wavelengths of light to include wavelengths as short as a fourth of the diameter of the particle. The light source may also be configured to emit light of multiple wavelengths.

The light detector may be configured to detect scattered light of different wavelengths in different regions of the detector. The light detector also may be configured to detect the scattered light in an angular direction substantially equal to an angular direction of propagation of the light. Alternatively, the light detector may be configured to detect the scattered light in an angular direction between an angular direction of propagation of light from the light source and an angular direction perpendicular to the propagation of the light.

It should be appreciated that the system described herein may be configured to detect any type of aerosol or chemical particle.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating the example embodiments.

FIGS. 10A-10D are schematics of alternative designs of the forward scattering particle detection system of FIG. 3 according to example embodiments.

DETAILED DESCRIPTION

A description of example embodiments follows.

Figure 1:
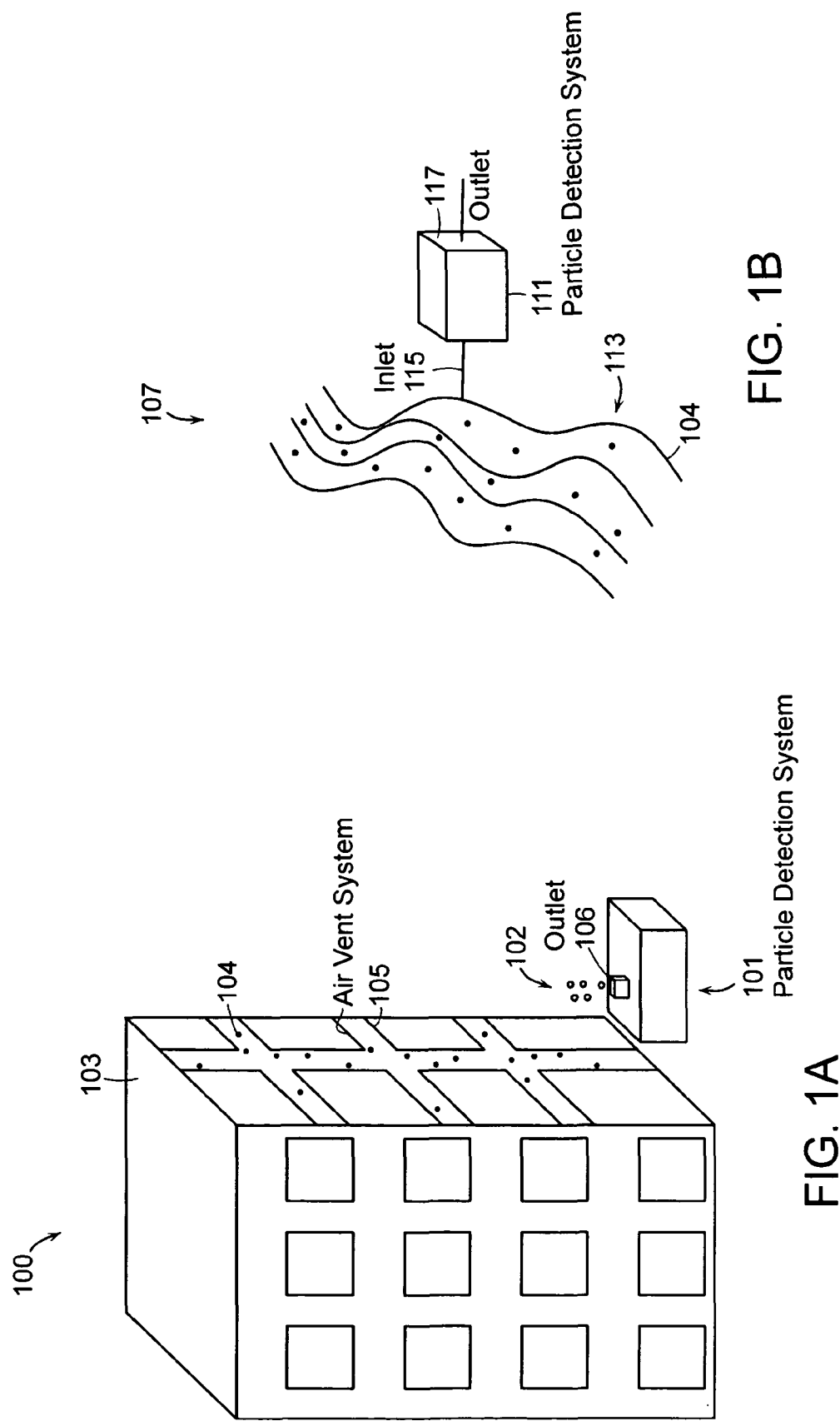
FIGS. 1A and 1B are diagrams with examples of particle detection systems.

FIG. 1A provides an overview example 100 of a particle detection system 101. The particle detection system 101 may be situated to detect particles 104 in an airvent system 105 of a building 103. The particle detection system 101 includes an inlet (not shown) in which an airflow enters the particle detection system 101. An outlet 106 of the particle detection system 101 may be used as a pathway to shunt the airflow if particles 102 detected are deemed unsafe for breathing. Otherwise, the airflow can continue into the airvent system 105.

As another example, a liquid stream may also need to be evaluated. For instance, a water reservoir may need to be continuously monitored to ensure harmful particles are not introduced into a water supply.

FIG. 1B provides an overview example 107 of a particle detection system 111 detecting particles 113 in a liquid stream 109. The particle detection system 111 may include an inlet 115 used to supply a sample of the liquid flow 109 to the particle detection system 111. Once the liquid flow 109 has been checked for a presence of foreign particles, an outlet 117 may be used to remove the sample from the particle detection system 111.

Figure 2:
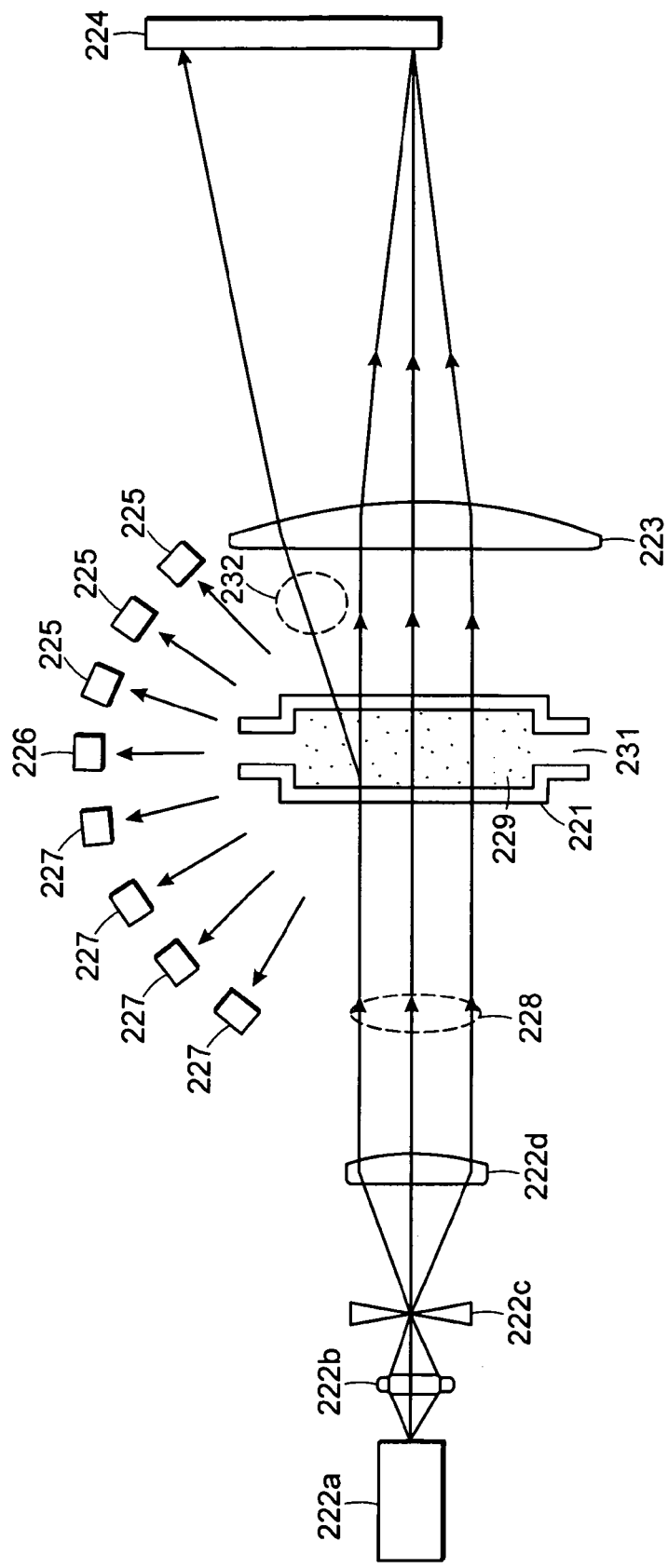
FIG. 2 is a schematic of an optical system of a conventional particle size analyzer.

FIG. 2 provides an example of the components of a prior art system used for analyzing particles. The system of FIG. 2 includes a laser source 222a configured to emit a laser beam onto a condenser lens 222b, spatial filter 222c, and a collimator lens 222d, resulting in collimated light 228. The collimated light 228 is configured to interfere with a number of particles 229, held in suspension within a sample volume 231, in order to produce a spatial light intensity distribution pattern of scattered light. Light 232 scattering in an angle smaller than 35° in a forward angle is condensed by a condenser lens 223 to form a scattering image on a ring detector 224 positioned at a focal point of the lens. Light scattered forwardly in a larger angle range (e.g., >35°) and light scattered laterally and rearwardly are detected by forward large angle scattered light sensors 225, sideward scattered light sensors 226, and rearward scattered light sensors 227, formed of independent light sensors, respectively.

The intensity distribution data of the light scattered by the particles 229 to be measured vary according to the sizes of the particles. Since the actual particles 229 to be measured include particles of different sizes, the intensity distribution data of the scattered light generated by the particles 229 to be measured become a superposition of the lights scattered from the respective particles. Analyzing the superpositioned light scattering provides data on the particle size distribution of the particles included in the sample volume. Note that the prior art point detection system illustrated in FIG. 2 requires the use of a single wavelength laser source and multiple detectors measuring multiple particles at one given time. Further note that the system of FIG. 2 is not capable of determining the absorption of the particles as it is difficult to directly measure the amount of light a particle absorbs due to the difficulty of separating the light scattered from the light absorbed.

In example embodiments of a particle detection system, a particle point detection system includes a single detector that may be configured to determine a particle absorption and/or chemical composition from data obtained from a single particle is disclosed. The particle absorption and/or chemical composition may be determined by analyzing an amount of light scattered by the particle. Furthermore, the example system presented herein may also be configured for "on-the-fly" particle detection. It should be appreciated that alternative embodiments may employ multiple detectors.

Figure 3:
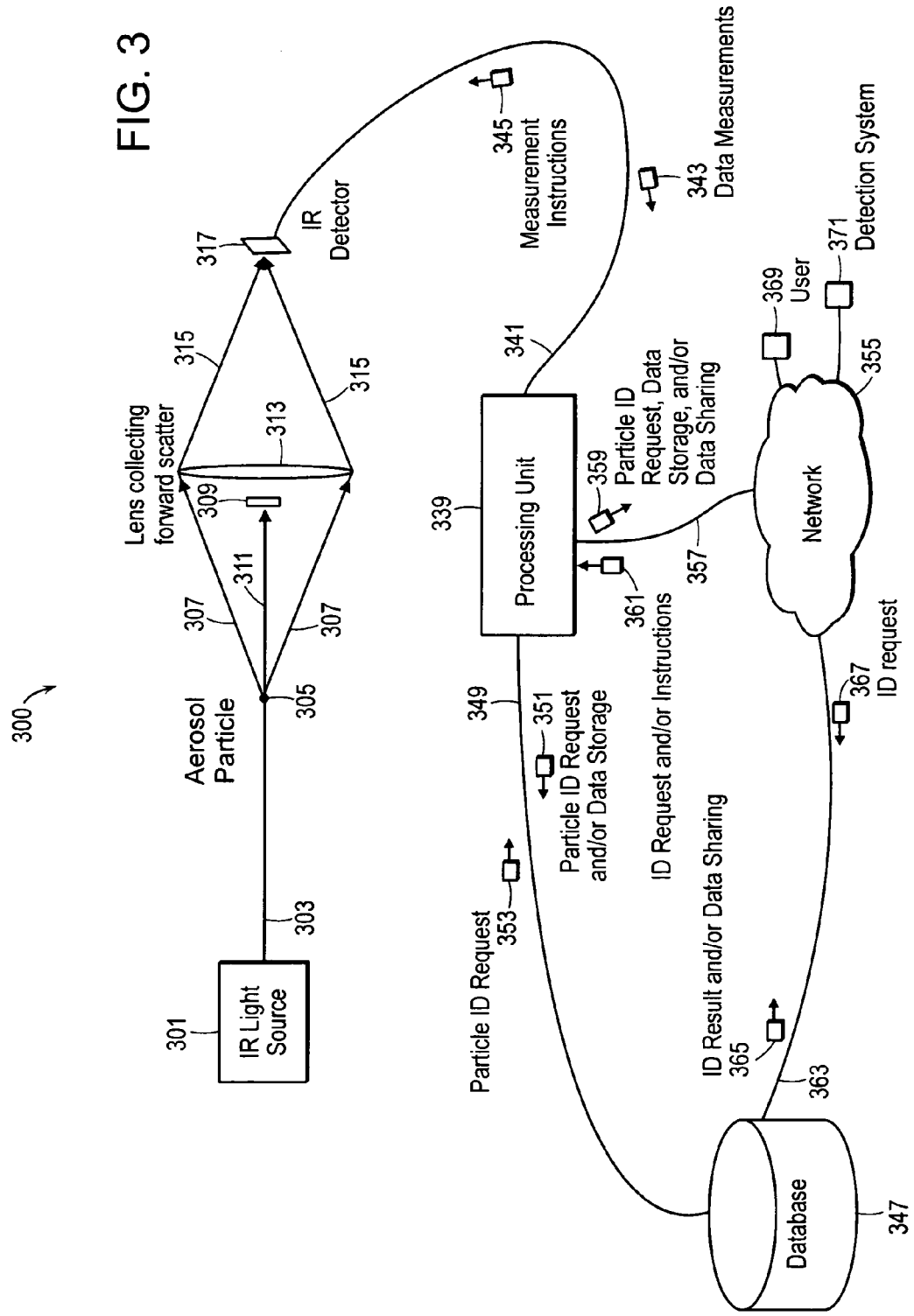
FIG. 3 is a schematic of a forward scattering particle detection system according to example embodiments.

FIG. 3 illustrates an example particle point detection system 300 according to example embodiments. The detection system 300 may measure size and absorption of a single particle or an ensemble of particles. The detection system 300 may include an infrared light source 301 that may be configured to emit a light beam 303. The light source 301 may be configured to emit light of multiple wavelengths in succession or simultaneously. The light beam 303 may illuminate a particle 305 traveling in a fluid stream, where the fluid may include air, water, vapor, or any other known liquid or gas. Upon illuminating the particle, diverging scattered light 307 may be produced. The scattered light 307 may be used to obtain a scattering spectrum that may provide characteristics of the illuminated particle as a function of measured intensity and wavelength.

A beam block 309 may be configured to block the light beam 311 upon particle illumination, such that a light detector 317 does not receive light directly from the light beam, therefore preventing saturation of the light detector 317. A focusing element 313 may be used to focus the scattered light 315 onto the light detector 317. Any form of light detection known in the art may be used as the light detector 317.

The configuration of the detection system 300 features forward scattering detection, where the scattered light 315 is detected in approximately the same direction of propagation as the light beam 303.

The light detector 317 may be coupled to a processing unit 339. The light detector 317 may be configured send data measurements 343 to the processing unit 339 in the form of an analog electrical signal. The processing unit 339 may be configured to determine physical properties of the particle as a function of the measured data and wavelength used to produce the light scattering.

The processing unit 339 may be configured to send measurement instructions 345 to the light detector 317 in the case that the light detector 337 includes an intelligent programmable configuration. The measurement instructions 345 may include, for example, on/off instructions or reading instructions. The light detector 317 and the processing unit 339 may be connected via a connection link 341. It should be appreciated that the connection link 341 may be a wired, optical, or wireless connection, or any other data transfer connection known in the art.

The processing unit 339 may also be connected to a database storage 347. The processing unit 339 may send the database storage 347 a particle identification request, and/or a data storage request 351. The data storage request 351 may include the data measurements 343, or representation thereof, provided by the light detector 317. The particle identification request may include a request to compare information stored in the database storage 347 with the obtained data measurements 343, optionally for the purpose of classifying and identifying the particles in the sample volume 327. The database storage 347 may send a particle identification result 353 to the processing unit 339. The particle identification result 353 may comprise a listing of possible particle matches with respect to the data measurements 343.

The processing unit 339 may also be coupled to a network 355. The processing unit 339 may send a particle identification request, a data storage request, and/or a data sharing request 359 to the network 355. The particle identification request and data sharing request 359 may be similar to the request 351 sent to the database storage 347. The data sharing request 359 may be a request to share data with a user 369 that may be connected to the network 355, or another detection system 371 that may be connected to the network 355. The network 355, or more specifically, a server or other network element (not shown) connected to the network 355, may also send a message 361 in the form of particle identification results, similar to the result 353 sent by the database storage 347, or instructions to the processing unit 339. The instructions 361 may comprise measurement instructions similar to the instructions 345 sent to the light detector 317.

The database storage 347 and the network 355 may also include a bidirectional data transfer connection 363. The database storage 347 may send identification results and/or a data sharing request 365 to the network 355. The network 355 may send an identification request 367 to the database storage 347. It should be appreciated that the data transfer connections 349, 357, and 363 between the processing unit and the data storage, the processing unit and the network, and the network and the data storage, respectively, may include or be supported by any data transmission link known in the art.

Once a scattering spectrum, or measured data, has been obtained, the physical properties of the particle may be determined. In an example embodiment, a method for detecting and classifying individual micron-sized particles is based on their infrared (IR) absorption spectra. The IR absorption spectra may result from vibrations of chemical or molecular bonds of the particle. These vibrations may occur naturally or as a result of the illumination of the particle.

Normally, scattered light intensity from an object (particle) decreases with increasing wavelength. In this context, anomalous scattering refers to a relatively sharp increase in scattering intensity as wavelength increases. This effect may be caused by a relatively rapid change in the real refractive index at wavelengths associated with an absorption peak, an inherent property of the particle material. Therefore, achieving discrimination between certain agent aerosols and natural background aerosols may be used to interrogate individual aerosol particles "on-the-fly" with a discrete set of IR wavelengths that, in effect, may provide an IR absorption spectrum of the particle material via the anomalous scattering signals. Many biological warfare (BW) and chemical warfare (CW) agent materials have distinctive IR spectrums, and may thus be characterized via an IR spectrum.

Currently, there are no comparable capabilities for determining aerosol absorption. It is generally not feasible to infer true absorption in either single particles or aerosol populations from direct extinction (transmission loss) measurements because: (a) significant wavelength, and particle size, shape, and composition dependencies of the elastic scattering are too complex to accurately model without a priori information, and (b) scattering losses from aerosols are typically the dominant contribution to extinction, so that small errors in determining the scattered energy translate into larger errors in estimating absorption. Consequently, absorption determination based attenuation measurements have been historically accomplished for aerosols only by first collecting them onto a filter substrate.

In example embodiments, a rapid, on-the-fly, aerosol point detection capability, comparable with fluorescence triggers currently employed, may be achieved with the development of a new approach to aerosol particle absorption determination, as a function of an anomalous scattering approach.

The anomalous scattering approach may be based on the connection between absorbed and scattered incident radiation results from a well-known fundamental relationship between the real and imaginary parts of any material's effective complex refractive index. Therefore, the proposed technique is quite general and leads to a new on-the-fly aerosol diagnostic technique for major constituent compositional analysis based on IR spectral absorption profiles, which are analogous to well-established conventional IR absorption spectroscopy for bulk materials.

Figure 4:
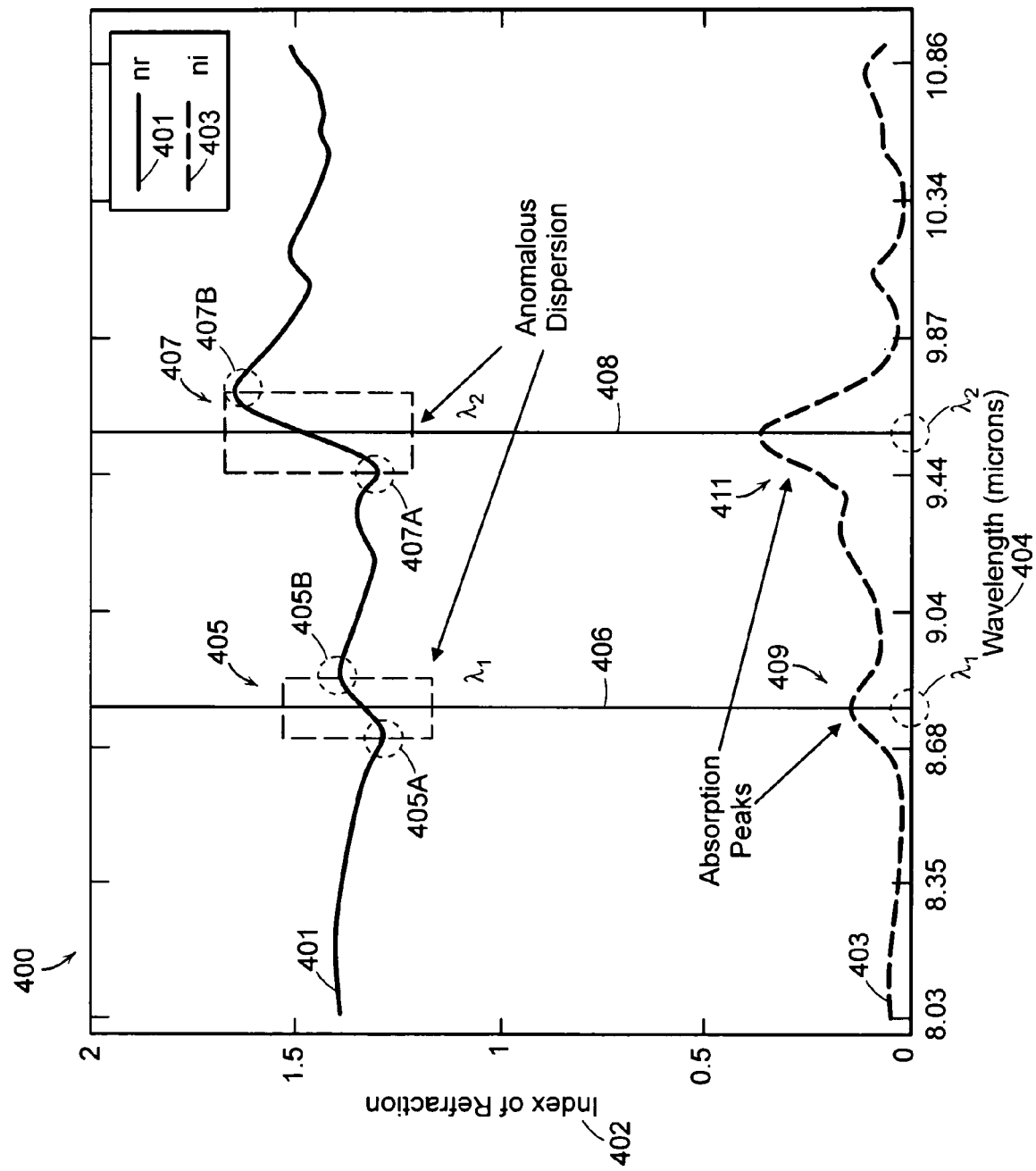
FIG. 4 is a graphical representation of the real and imaginary indices of refraction of propylene glycol.

FIG. 4 illustrates the real 401 and imaginary 403 parts of the refractive index (y-axis 402) of a propylene glycol particle for a 8-11 μm wavelength region (x-axis 404). Within this wavelength range a propylene glycol may have two prominent absorption features 409 and 411 that may be seen as peaks at 8.75 μm and 9.55 μm, $\lambda_1$ and $\lambda_2$, respectively, in the imaginary index of refraction, $n_i$ 403, and highlighted with vertical lines 406 and 408, respectively, running the height of the plot. Associated with peaked regions 409 and 411 in the imaginary part of the index of refraction 403 are regions of anomalous dispersion 405 and 407, respectively, in the real part of the index of refraction, $n_r$ 401. The anomalous dispersion region 405 may be defined by points 405a and 405b, whose relation reflect an increase in the real part of the index of refraction within a region of increasing wavelength. Similarly, the anomalous dispersion region 407 may be defined by points 407a and 407b.

Since the anomalous dispersion in the real part of the index of refraction is associated with the absorption peaks in the imaginary part of the index of refraction, the scattering spectrum may be analyzed to determine the absorption peaks.

Figure 5A:
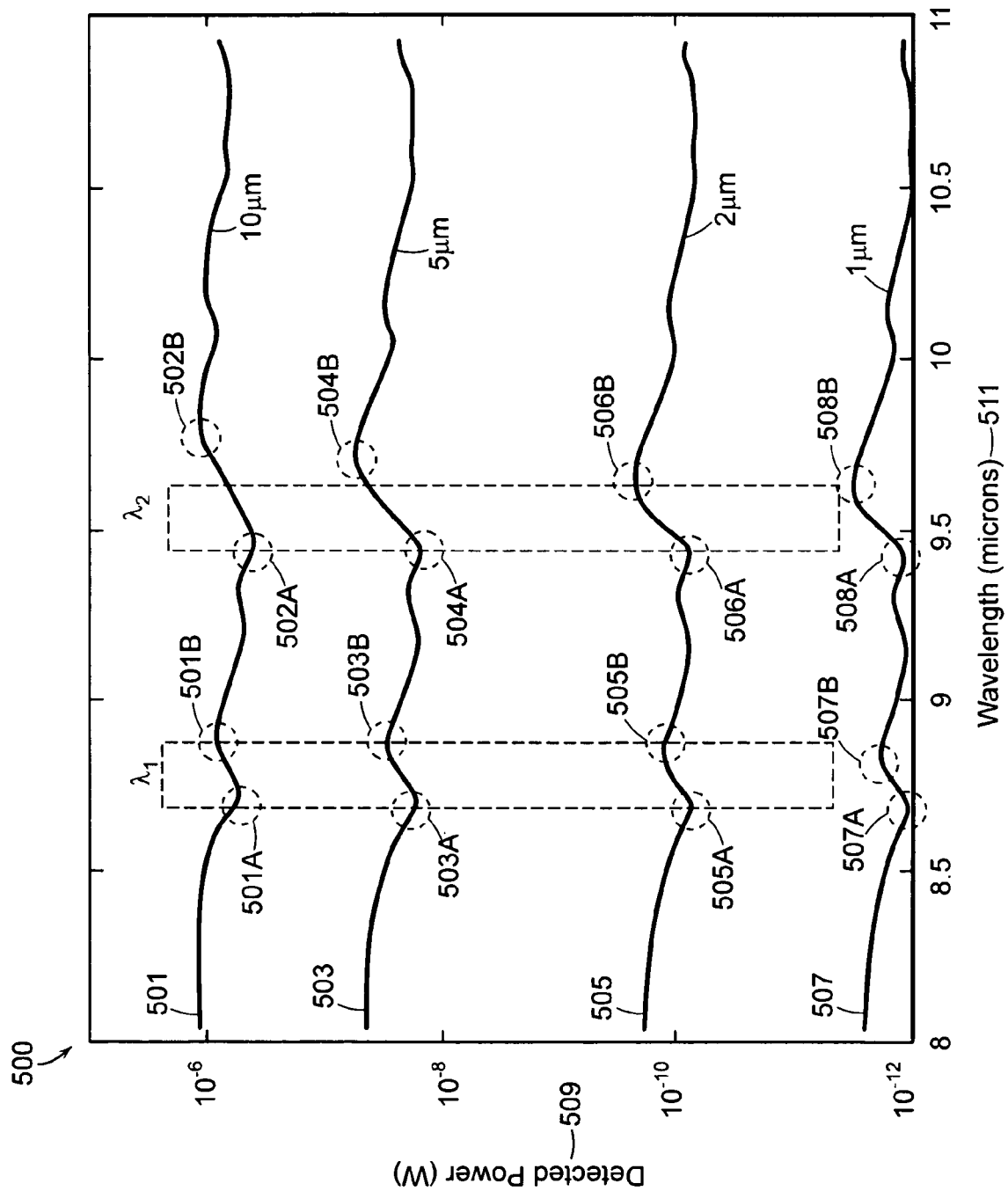
FIG. 5A is a graphical representation of detected scattered light versus wavelength obtained using the system of FIG. 3 according to example embodiments.
Figure 5B:
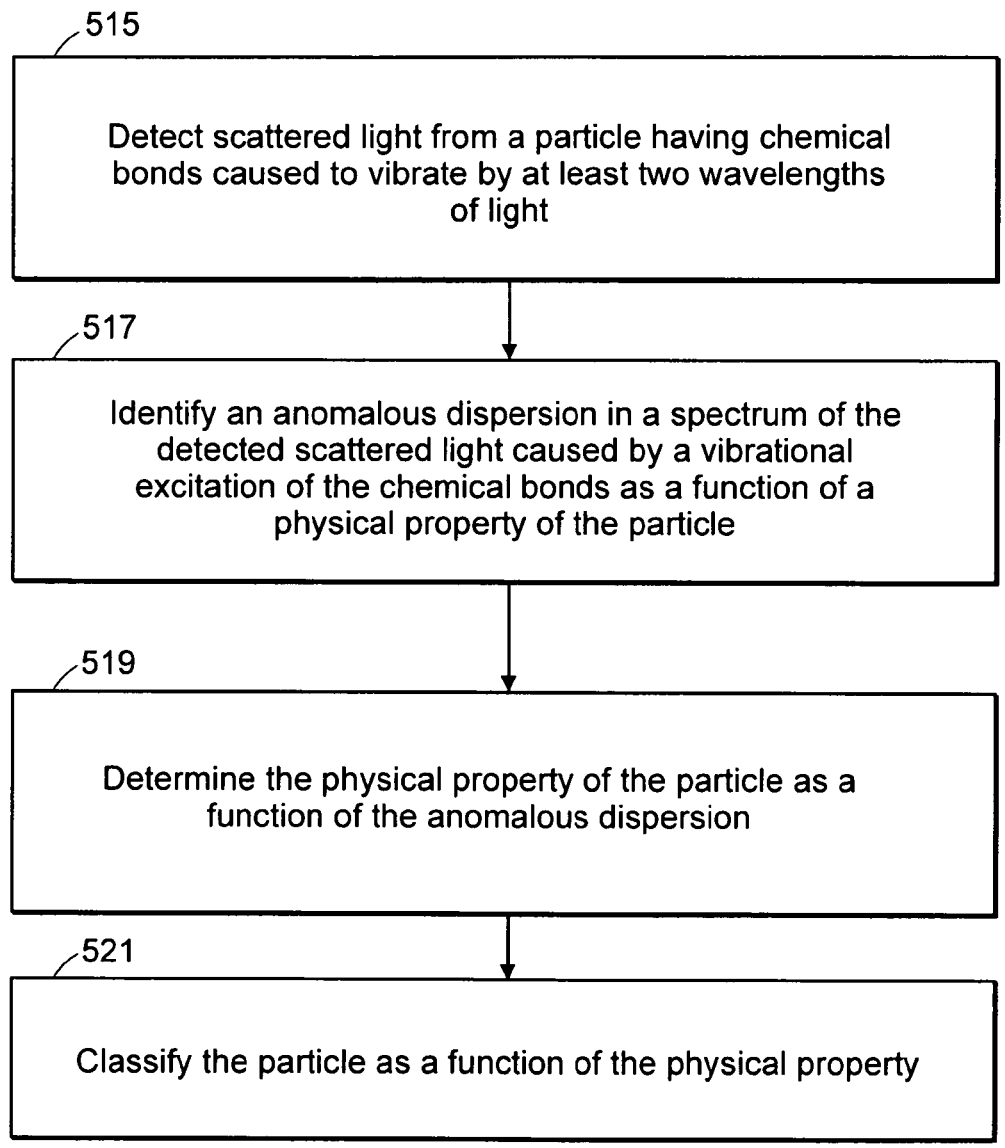
FIG. 5B is a flow diagram of example operational steps used in analyzing the data of FIG. 5A according to example embodiments.
Figure 6:
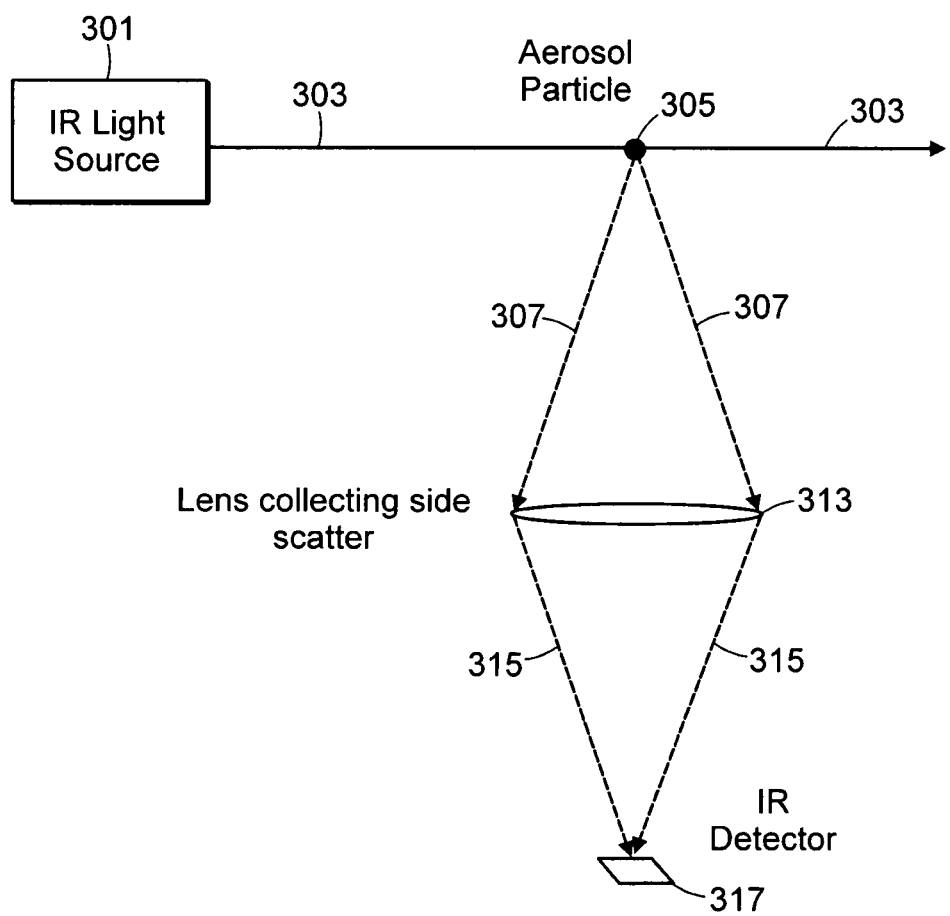
FIG. 6 is a schematic of a side scattering particle detection system according to example embodiments.
Figure 7:
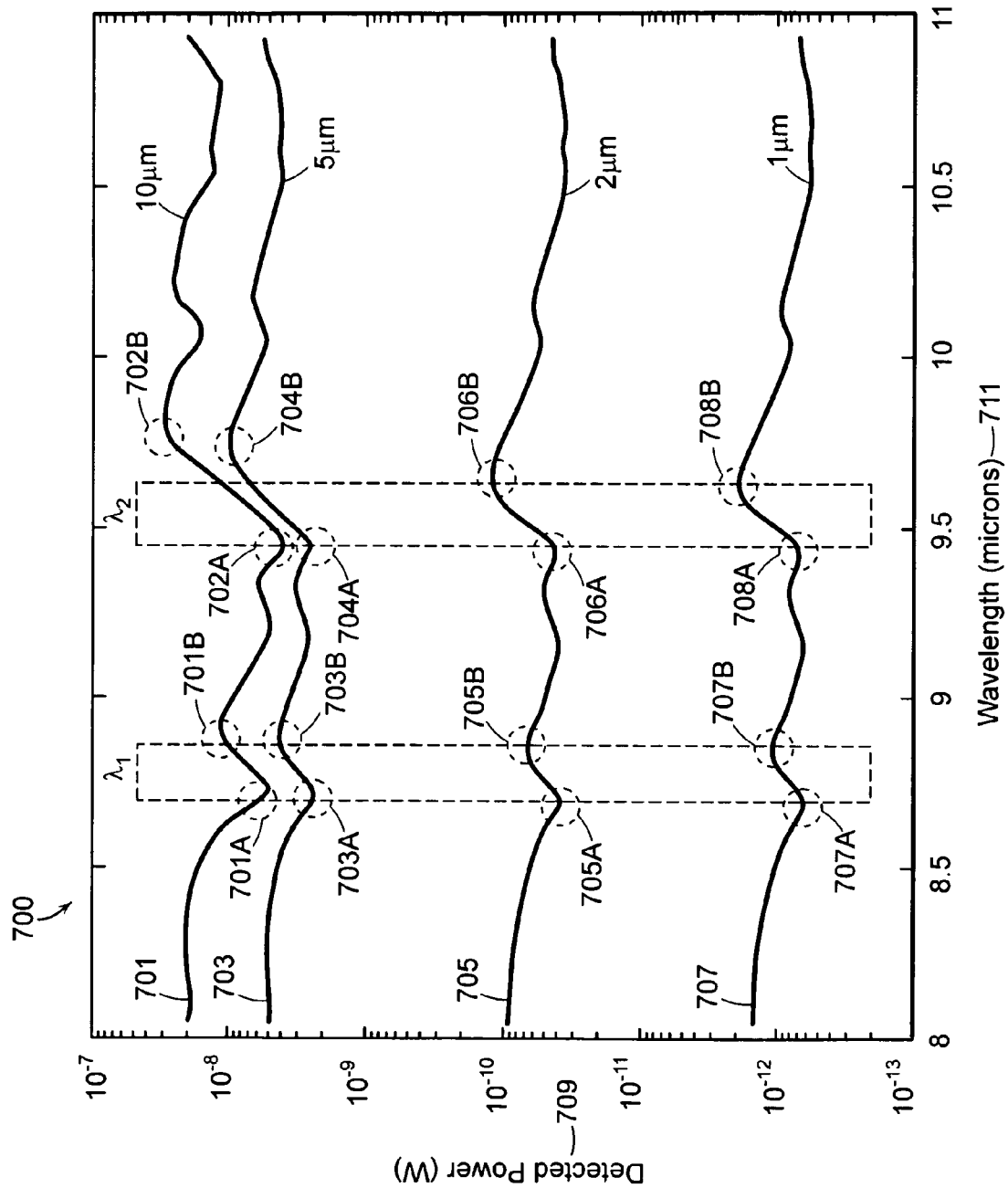
FIG. 7 is a graphical representation of detected scattered light versus wavelength obtained using the system of FIG. 6 according to example embodiments.
Figure 8:
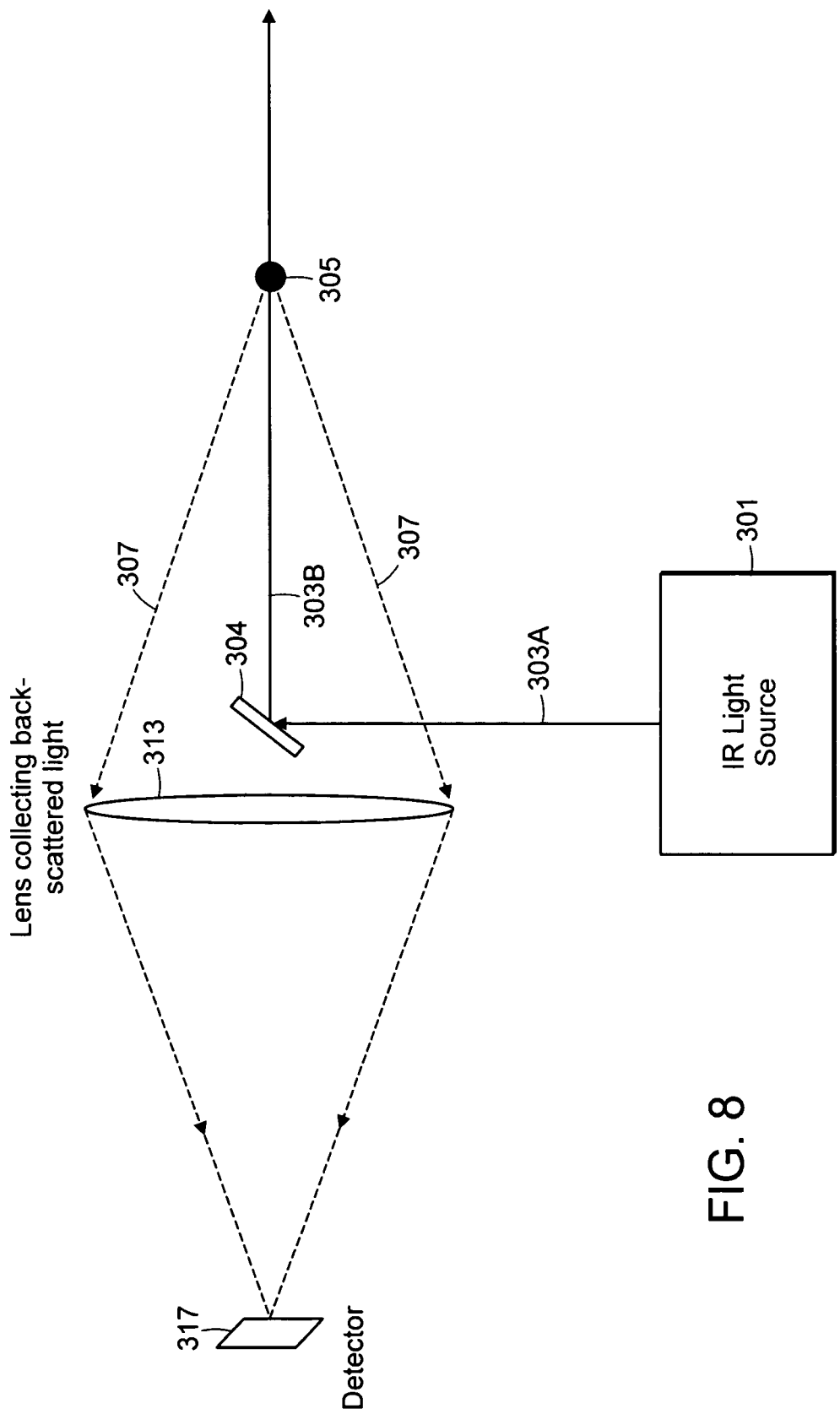
FIG. 8 is a schematic of a near back scattering particle detection system.
Figure 9:
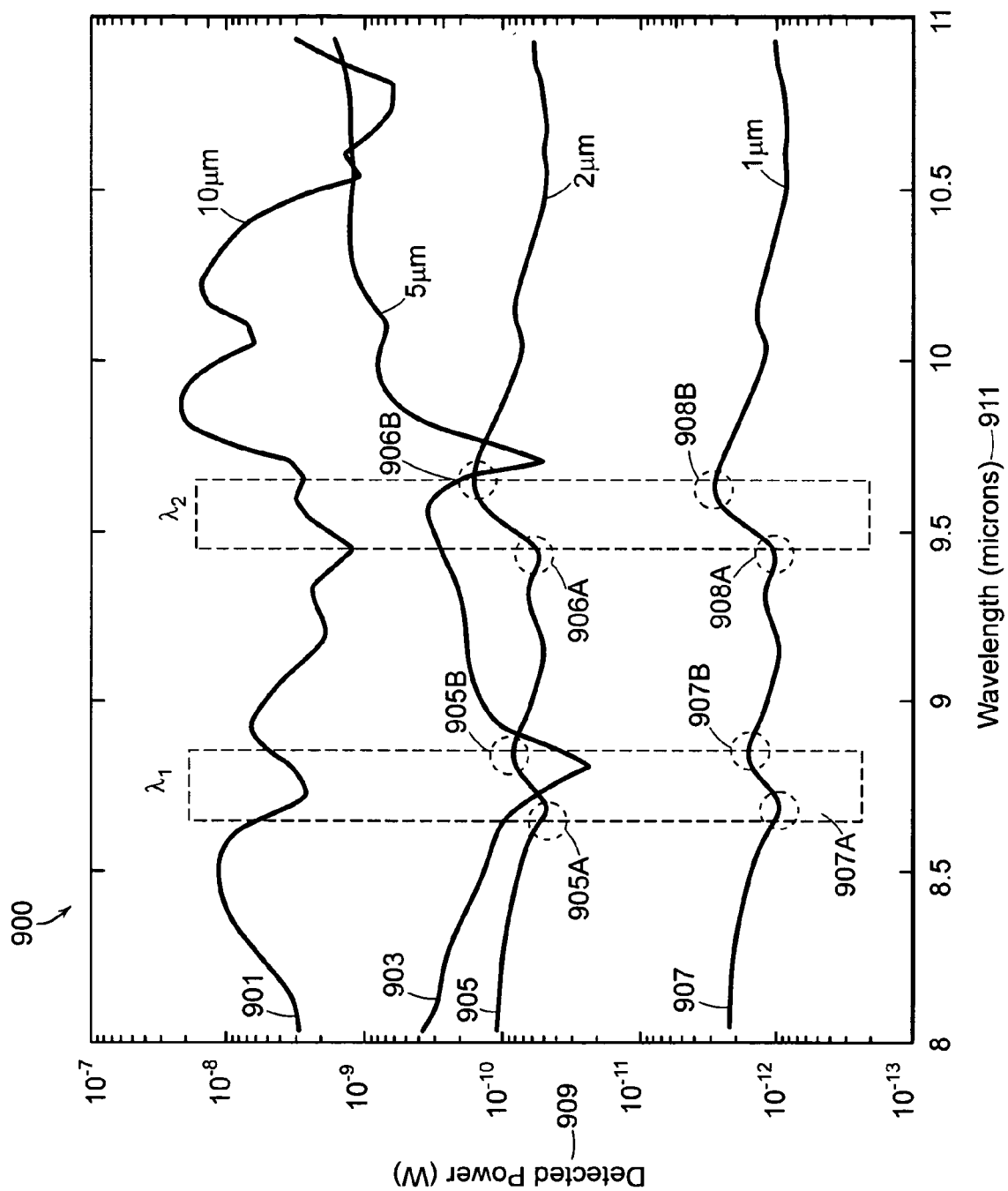
FIG. 9 is a graphical representation of detected scattered light versus wavelength obtained using the system of FIG. 8.

FIG. 5A illustrates the power detected 509 (y-axis) versus the wavelength 511 (x-axis) for propylene glycol spherical droplets for a scattering configuration similar to the system illustrated in FIG. 3. FIG. 5B shows a flow diagram of example operations that may be taken in the evaluation of data shown in FIG. 5A. Each trace 501, 503, 505, and 507 represents a single particle size 10, 5, 2, and 1 microns in diameter, respectively. As illustrated in FIG. 5A, each trace 501-507 includes two prominent anomalous dispersion regions associated with wavelengths $\lambda_1$ and $\lambda_2$. The peaks in the scattered light profile may be the result of vibrations of chemical bonds included in the particle due to absorption properties of the particle (515).

As explained in relation to FIG. 4, the anomalous dispersion regions may be identified by regions of increasing detected power with increasing wavelengths (517). For example, within trace 501, obtained with particles including a diameter of 10 microns, there is an increased power detection between points 501A-501B and 502A-502B defining absorption peaks at wavelengths $\lambda_1$ and $\lambda_2$, respectively. Within trace 503, obtained with particles including a diameter of 5 microns, there is an increase in power detected between points 503A-503B and 504A-504B defining absorption peaks at wavelengths $\lambda_1$ and $\lambda_2$, respectively. Within trace 505, obtained with particles including a diameter of 2 microns, there is an increased power detection between points 505A-505B and 506A-506B defining absorption peaks at wavelengths $\lambda_1$ and $\lambda_2$, respectively. Within trace 507, obtained with particles including a diameter of 1 micron, there is an increased power detection between points 507A-507B and 508A-508B defining absorption peaks at wavelengths $\lambda_1$ and $\lambda_2$, respectively.

As can be seen in FIG. 5A, the scattering spectrum encodes the absorption peaks as regions of anomalous scattering and is nearly independent of particle size as the peaks for traces 501-507 are roughly within the same wavelength range $\lambda_1$ and $\lambda_2$.

It should be appreciated however that for smaller particle sizes, the scattering mirrors the anomalous dispersion of the index of refraction. As the particle size increases the minimum in the scattering signal versus wavelength slightly red shifts. For example, the regions of increased detection 502A-502B and 504A-504B of traces 501 and 503, respectively, are slightly out of the wavelength range $\lambda_2$. Eventually, when the particle size is much greater than the wavelength of light, the scattering minimum, or wavelength at which the second derivative with respect to wavelength of the scattering is greater than it is for neighboring wavelengths, may coincide with the peak in absorption.

However, when the particle size is much greater than the wavelength of light, the particle size also contributes to the scattering spectrum. For cases where the particle size is more than four times the wavelength, the scattered light spectrum has minima and maxima that result from destructive and constructive interference of different paths the light can take through the particle. In this regime the association between the spectrum of the index of refraction, regions of anomalous dispersion, and the associated regions of anomalous scattering are not a strict dependence. In this regime of particle size to scattering wavelength, the scattering spectrum may not a reliable indicator of the absorption features of the aerosol particle.

Once the anomalous dispersion regions have been identified, various physical properties of the particle may be determined (519). These physical properties may include, but are not limited to, a chemical composition of the particle or an absorption region. Utilizing the physical properties of the particle, a classification, or discrimination, of the particle may be made (521).

It should be appreciated that although propylene glycol spherical droplets were used in obtaining the data of FIG. 5A any other particle may be classified using embodiments presented herein. For example a complex particle, such as a DNA strand may be classified.

FIG. 6 illustrates an alternative detection configuration according to example embodiments. The detection system of FIG. 6 utilizes a side scattering detection method. The side scattering system may include a light source 301 that may be configured to emit a light beam 303. The light beam 303 may interfere with a particle 305, thereby creating a diverging light scattering. A lens 313 may be position in a location approximately traverse with respect to the direction of propagation of the laser beam 303. The location of the lens 313 allows for a diverging side scattering 307 to be focused onto an infrared detector 317. It should be appreciated that the processing unit, network, and database connections illustrated in FIG. 3 may also be applied to the system of FIG. 6.

FIG. 7 illustrates the power detected 709 (y-axis) versus the wavelength 711 (x-axis) for propylene glycol spherical droplets. The measured data illustrated in FIG. 7 may be obtained using a detection configuration similar to the system illustrated in FIG. 6. Each trace 701, 703, 705, and 707 represents a single particle size 10, 5, 2, and 1 microns in diameter, respectively. As illustrated in FIG. 7, each trace 701-707 includes two prominent anomalous dispersion regions associated with wavelengths $\lambda_1$ and $\lambda_2$. The anomalous dispersion regions for trace 701 are labeled as 701A-701B and 702A-702B, corresponding to wavelengths $\lambda_1$ and $\lambda_2$, respectively. The anomalous dispersion regions for trace 703 are labeled as 703A-703B and 704A-704B, corresponding to wavelengths $\lambda_1$ and $\lambda_2$, respectively. The anomalous dispersion regions for trace 705 are labeled as 705A-705B and 706A-706B, corresponding to wavelengths $\lambda_1$ and $\lambda_2$, respectively. The anomalous dispersion regions for trace 707 are labeled as 707A-707B and 708A-708B, corresponding to wavelengths $\lambda_1$ and $\lambda_2$, respectively.

As is illustrated in FIG. 7, a side scattering detection system provides a light spectrum that may be unreliable as the size of the particle under investigation increases. For example, in the traces 701 and 703 associated with particles featuring a diameter size of 10 and 5 microns, respectively, the anomalous dispersion region associated with the wavelength $\lambda_2$ is red shifted in comparison to the traces 705 and 707. The red shifting may be caused by a lack of scattered light in the side scattering direction. The lack of increase in scattering from 10 micron-diameter particles from those of 5 micron-diameter may be due to the scattering pattern becoming more biased towards the forward direction with increasing particle size.

However, it should be appreciated that the scattering spectrum of FIG. 7 is still dominated by the absorptive features of the aerosol particle. For the smaller particle sizes the minimum in the scattering spectra still coincide with the minimum in the real part of the refractive index.

FIG. 8 illustrates yet another alternative detection configuration. The detection system of FIG. 8 utilizes a near back-scattering geometry. The near back-scattering system may include a light source 301 that may be configured to emit a light beam 303A. The light beam 303A may be reflected and redirected by a mirror 304. The redirected beam 303B may interfere with a particle 305 traveling in a same direction as the beam 303B, thereby creating a backward diverging light scattering 307. A lens 313 may be position in a location approximately along the same axis with respect to the direction of propagation of the laser beam 303B. The location of the lens 313 allows for the backward diverging scattering 307 to be focused onto an infrared detector 317. It should be appreciated that the processing unit, network, and database connections illustrated in FIG. 3 may also be applied to the system of FIG. 8.

FIG. 9 illustrates the power detected 909 (y-axis) versus the wavelength 911 (x-axis) for propylene glycol spherical droplets for a scattering configuration similar to the system illustrated in FIG. 8. Each trace 901, 903, 905, and 907 represents a single particle size 10, 5, 2, and 1 microns in diameter, respectively. As shown in FIG. 9, the spectrum associated with a near back-scattering system may be particle size dependent. For example, the traces 905 and 907 corresponding to particle having a diameter size of 2 and 1 microns, respectively, have well defined regions of anomalous dispersion. The anomalous dispersion regions of trace 905 are labeled as 905A-905B and 906A-906B for wavelengths $\lambda_1$ and $\lambda_2$, respectively. The anomalous dispersion regions of trace 907 are labeled as 907A-907B and 908A-908B for wavelengths $\lambda_1$ and $\lambda_2$, respectively.

Conversely, the traces 901 and 903 associated particles having diameter sizes of 10 and 5 microns, respectively, are greatly red shifted and include large fluctuations in detected power. Thus, in detection systems featuring a near backscattering geometry, as the diameter size of a particle increases, the reliability of the measured data may decrease.

FIGS. 10A-10D illustrate alternative embodiments of the particle detection system according to example embodiments. The forward scattering detection system of FIG. 10A includes a light source 319 that may be configured to simultaneously emit parallel light beams of different wavelengths 321. An aerosol particle 305 may be configured to travel in a fluid stream in a direction approximately traverse to the direction of propagation of the light beams 321. The resulting diverging scattered light 307 may include a temporal dependence that corresponds to the scattering spectrum. A lens 313 may be used to collect and focus the scattered light 307 onto an infrared photodetector 317. The focused light 327 may include multiple focus points where each point may correspond to a different wavelength. A beam block 309 may be used to prevent the laser beams 321 from reaching and saturating the photodetector 317.

Figure 10A:
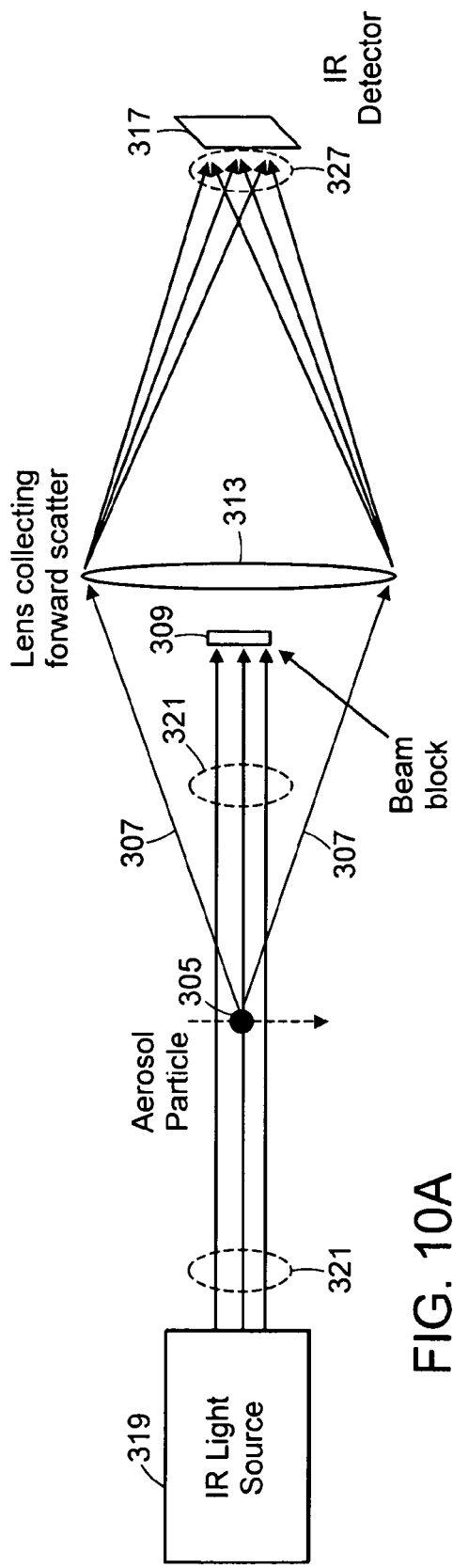
Figure 10B:
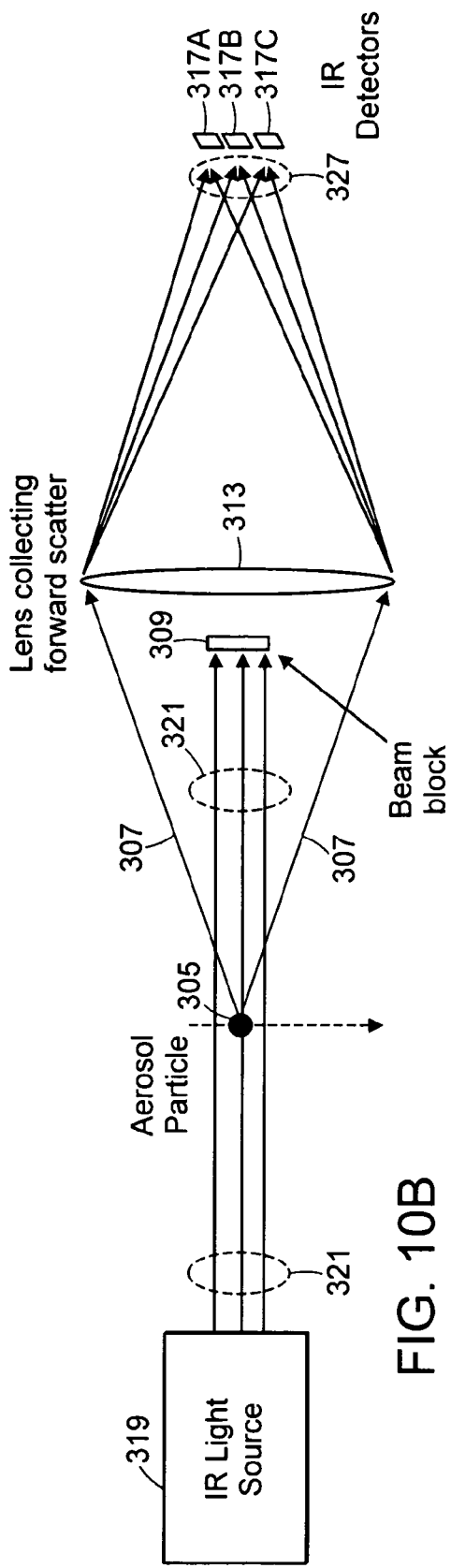

FIG. 10B illustrates an alternative design where the infrared detector includes an array of photodetectors 317A-317C, where each detector may be configured to receive light of a corresponding wavelength.

FIG. 10C illustrates an alternative design where the light source 331 may be configured to emit overlapping beams of multiple wavelengths 303 through a technique known as wavelength combining. Upon intersecting with the particle 305 traveling in a direction traverse to the direction of propagation of the beam 303, scattered light 307 may be produced. This alternative design includes an optical system including a pair of collecting lenses 313A and 313B and an optical dispersing element 329. The optical dispersing element, such as a prism or a grating 329 may be located between the two collecting lenses 313A and 313B and may be used to demultiplex the multi-wavelength scattered light. Similarly to the system illustrated in FIG. 10B, the demultiplexed scattered light may be focused onto an array of detectors 317A-317C, where each detector may be configured to detect light of a single wavelength.

FIG. 10D illustrates another alternative design that is similar to the design illustrated in FIG. 10C with the exception that the light source 331 is configured to produce an overlapping beam where the different wavelengths may be modulated in time so that the light scattering may be generated from one wavelength at any give time. Therefore, the all the scattered light may be focused in a same location on the infrared detector 317, thus eliminating the need for multiple detectors and thereby allowing for a reduction the necessary detection size.

It should be appreciated that the detection systems of FIGS. 10A-10D may also include the processing unit, network, and database connections illustrated in FIG. 3.

It should also be appreciated that the embodiments described herein may be used regardless of a particle's shape. Thus, the shape of a particle does not impose limitations on the example embodiments presented. Furthermore, it should be appreciated that the embodiments described herein may be used to detect any known aerosol or chemical particle.

It should be understood that the process, disclosed herein, may be implemented by a computer controlled machine using instructions implemented in hardware, firmware, or software. If implemented in software, the software may be stored on any form of computer readable medium, such as random access memory (RAM), read only memory (ROM), compact disk read only memory (CD-ROM), and so forth. In operation, a general purpose or application specific processor loads and executes the software in a manner well understood in the art. It should also be appreciated that the embodiments presented herein may be employed in general spectroscopy systems. For example, the system presented may be employed in terahertz spectroscopy.

While this invention has been particularly shown and described with references to example embodiments thereof, it will be understood by those skilled in the art that various changes in form and details may be made therein without departing from the scope of the invention encompassed by the appended claims.

What is claimed is:

1. A method of determining a physical property of a particle, the method comprising:
   illuminating a particle with infrared light;
   detecting elastically scattered light from the particle having a size smaller than or equal to the wavelength of the scattered light, having chemical structures, to determine an elastic scattering spectrum of the particle;
   identifying at least two regions of the elastic scattering spectrum of the particle representative of vibrations of the chemical structures by identifying regions of non-decrease of intensity of scattered light in regions of the spectrum of increasingly longer wavelengths;
   determining an absorption spectrum of the particle based on the at least two regions of the elastic scattering spectrum of the particle, the absorption spectrum defined by respective absorption peaks spectrally located within respective regions of the at least two regions of the elastic scattering spectrum, and the respective absorption peaks corresponding to respective peaks in an imaginary part of a refractive index of the particle; and
   determining the physical property of the particle based on the absorption spectrum of the particle based on the at least two regions of the elastic scattering spectrum.

2. The method of claim 1 further including classifying the particle as a function of the physical property.

3. The method of claim 1 wherein the physical property of the particle is a chemical composition.

4. The method of claim 1 wherein the physical property of the particle is an absorption region.

5. The method of claim 1 wherein:
   illuminating the particle with the infrared light includes using a light source; and
   detecting the scattered light includes detecting in an angular direction between an angular direction of propagation of light from the light source and an angular direction perpendicular to the propagation of light.

6. The method of claim 1 wherein:
   illuminating the particle with infrared light includes using a light source; and
   detecting the scattered light includes detecting in an angular direction substantially equal to an angular direction of propagation of light from the light source.

7. The method of claim 1 wherein illuminating the particle with infrared light includes using wavelengths greater than 2.5 µm.

8. The method of claim 1 wherein the particle is a single particle and determining the physical property of the particle is performed by analyzing the scattered light produced solely by the single particle.

9. The method of claim 1 wherein the particle is a complex particle and the at least two regions represent anomalous dispersion caused by a vibrational excitation including energies less than 0.5 eV.

10. The method of claim 9 wherein the complex particle is a DNA strand.

11. The method of claim 1 further including the chemicals bonds physically interacting via vibrations with vibrational excitation energies of less than 0.5 eV.

12. The method of claim 1 further including reporting the physical property of the particle by way of a machine-to-human interface or a signal transmitted via a communications network.

13. The method of claim 1 wherein the particle is an aerosol particle.

14. The method of claim 1 wherein the particle is in a fluid flow.

15. The method of claim 1, wherein determining the physical property of the particle includes comparing the absorption spectrum of the particle with one or more absorption spectra of known particles.

* * * * *